United States Patent
Graze et al.

(10) Patent No.: US 8,885,036 B2
(45) Date of Patent: Nov. 11, 2014

(54) PROCESS, LIGHTING EQUIPMENT AND SYSTEM FOR THE OPTICAL DETECTION OF MOVING OBJECTS

(75) Inventors: Bernd Graze, Graz (AT); Josef Fruehwirth, Graz (AT)

(73) Assignee: EKV di Kerschhaggl GmbH, Raaba (AT)

( * ) Notice: Subject to any disclaimer, the term of this patent is extended or adjusted under 35 U.S.C. 154(b) by 1019 days.

(21) Appl. No.: 12/749,167

(22) Filed: Mar. 29, 2010

(65) Prior Publication Data

US 2010/0245559 A1  Sep. 30, 2010

(30) Foreign Application Priority Data

Mar. 30, 2009 (AT) .................. A 501/2009

(51) Int. Cl.
*H04N 7/18* (2006.01)
*H04N 9/47* (2006.01)
*B07C 5/342* (2006.01)
*G01N 21/85* (2006.01)

(52) U.S. Cl.
CPC .............. *G01N 21/85* (2013.01); *B07C 5/3422* (2013.01)
USPC ........................................................ 348/86

(58) Field of Classification Search
CPC ......... H04N 7/18; B65B 19/28; G01B 11/022
USPC ........................................................ 348/86
See application file for complete search history.

(56) References Cited

U.S. PATENT DOCUMENTS

| | | | | |
|---|---|---|---|---|
| 5,750,985 A | * | 5/1998 | Suzuki | 250/234 |
| 7,345,698 B2 | * | 3/2008 | Abbott et al. | 348/86 |
| 7,698,068 B2 | * | 4/2010 | Babayoff | 702/19 |
| 2004/0223053 A1 | * | 11/2004 | Gladnick et al. | 348/79 |
| 2006/0082837 A1 | * | 4/2006 | Hiroe et al. | 358/448 |

FOREIGN PATENT DOCUMENTS

| | | |
|---|---|---|
| AT | 004 889 U1 | 12/2001 |
| AT | 410 847 B1 | 8/2003 |
| AT | 503036 A4 | 7/2007 |
| AT | 505 671 A4 | 3/2009 |

* cited by examiner

*Primary Examiner* — Chikaodili E Anyikire
(74) *Attorney, Agent, or Firm* — Workman Nydegger

(57) ABSTRACT

A process for the optical detection of moving objects comprises:
  illuminating the object either
    with light pulses having different intensities and/or pulse durations, or
    with light pulses optionally having different intensities and/or pulse durations, and
    with secondary light (SL) which induces an optically detectable secondary effect;
  taking images of the object under different illuminations with a monochromatic optical area sensor organized line by line;
  reading out and temporarily storing at least so many lines of each image as there are different illuminations, with the read-out lines having a line pitch relative to each other,
  sequentially combining lines from the images taken to form combination lines, with the lines combined with each other having the line pitch or a multiple thereof, respectively; and
  assembling the combination lines into a combinatory overall picture.

23 Claims, 4 Drawing Sheets

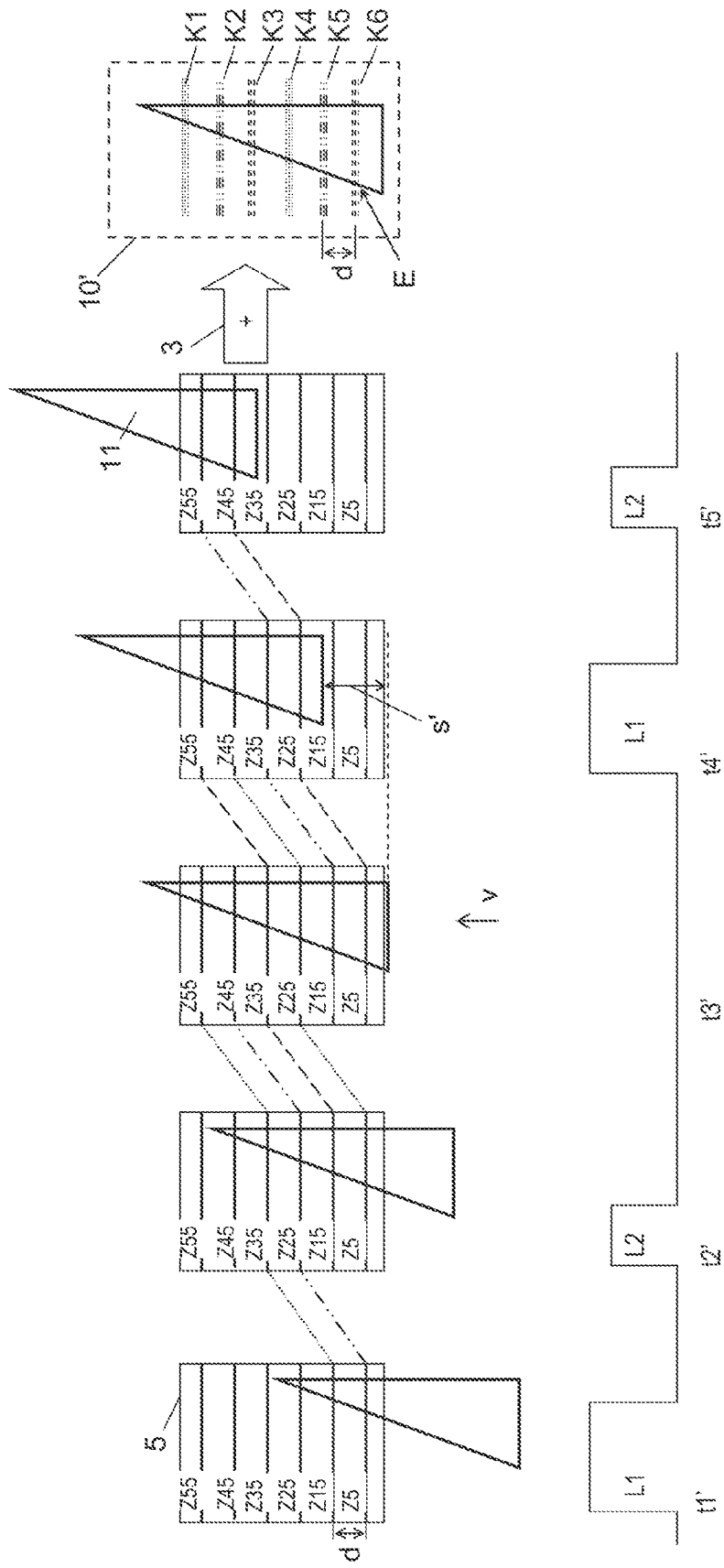

PROCESS, LIGHTING EQUIPMENT AND SYSTEM FOR THE OPTICAL DETECTION OF MOVING OBJECTS

The invention relates to a process, a lighting equipment and a system for the optical detection of objects moved at a conveying speed.

The detection and subsequent sorting of bulk materials with colour cameras is an established method. A common embodiment variant is described, for example, in Patent AT 410847. This technology is used in particular in the recycling field. In doing so, a transmitted light detection and a sorting are predominant in which glass and transparent synthetic products are processed by radiating light through them, collecting the light passing through by means of the colour camera and analyzing it. In this technology, labels on the transparent glass and plastic parts are, for example, a large obstacle so that costly mechanical methods, see, e.g., AT 503036 B1, are even employed for their removal in a prestage of the process. However, for improving the yield, it is absolutely desirable that transparent objects are identified although non-transparent foreign matters, such as labels, stick to them.

Furthermore, fluorescent tube systems or LED-based lighting systems (disclosed, e.g., in utility model AT 004889U1) are also used nowadays. The advances in optical technology provide colour cameras with higher and higher line scanning rates which, however, in turn require shorter and shorter illumination times and thus higher luminances for illuminating the objects to be detected. The high luminances required for systems with line scanning rates of 4-20 kHz, which are already prior art or will be available in the near future, can no longer be achieved with fluorescent tubes or thermal illuminants. Therefore, it has already been suggested that systems be equipped with light emitting diodes (LEDs) as illuminants in order to increase the luminance. Beam focussing optical systems in combination with a generation of white light via blue LEDs with yellow fluorescent dyes (so-called white light LEDs) have become established as standard in this field. However, due to the inefficient colour conversion, this type of illumination requires an active cooling, which is accomplished, for example, by water coolings in a costly manner.

Colour cameras with colour filters on the optically sensitive elements (pixels) or 3-chip cameras are today used as standard technology in connection with white light illumination, wherein one chip each is sensitive to one of the three primary colours red, green, blue. Furthermore, the demand made on the resolution and hence the number of pixels are getting larger and larger. Today, more than 1000 colour triples are already standard, and developments are aimed at raising the limit by one order of magnitude. This requires a further reduction in pixel size, which, in turn, further increases the demands made on the luminance of the lighting equipments, and also a decrease in the quality of the colour filters, which are questionable, anyway. In 3-chip cameras, the required optical splitting of the optical paths for separating the colour components and the adjustment of the sensors relative to each other are to be assessed as critical.

However, even with such modern equipments, the identification quality is still unsatisfactory, in particular as regards the differentiation of dark, opaque glass and plastic parts from ceramics, stones or porcelain. An as yet unsolved problem is the insufficient dynamic range of today's camera systems which often leads to faulty identifications, for example, if colourless glass is mixed with dark glass and non-transparent materials in the material stream. Furthermore, it would also be desirable to be able to differentiate between different types of the same basic material, for example, lead glass in a glass stream.

Thus, the need for an improved process for the optical detection of moving objects still exists which provides a high quality of identification at high conveying speeds of the objects to be detected. Such a process should be able to get by with lighting equipments which provide comparatively low luminances, but, at the same time, should also be able to handle high luminance conditions, i.e., a high luminance dynamic range.

The present invention is based on the problem of providing a process, a lighting equipment and a system for the optical detection of moving objects which overcomes the disadvantages of the prior art illustrated above.

This problem is solved by a process for the optical detection of moving objects having the characterizing features of claim 1, a lighting equipment having the characterizing features of claim 11 and a system for the optical detection of moving objects having the characterizing features of claim 16. Advantageous embodiments and further features of the present invention become apparent from the subclaims and the subsequent specification.

According to the invention, a monochrome sensor is used. The object is illuminated with a sequence of light pulses from at least one pulsed light source. In addition, the object can be illuminated with secondary light from a secondary light source the light of which induces an optically detectable secondary effect in the object. Light pulses may exhibit different intensities and/or different pulse durations.

Thus, the following variants of illuminating the objects with light are provided:
a) Illuminating the objects with a sequence of light pulses from at least one pulsed light source, with light pulses having different intensities and/or different pulse durations.
b) Illuminating the objects with a sequence of light pulses from at least one pulsed light source, with all light pulses having identical intensities and pulse durations. Additional illumination of the objects with secondary light from a secondary light source the light of which induces an optically detectable secondary effect in objects.
c) Illuminating the objects with a sequence of light pulses from at least one pulsed light source, with at least some of the light pulses differing from each other in light intensity and/or pulse duration. Additional illumination of the objects with secondary light from a secondary light source the light of which induces an optically detectable secondary effect in objects.

With every light pulse, an image of the object is taken and temporarily stored with the monochromatic area sensor. In illumination variants b and c, an image of the object is additionally taken by the monochromatic area sensor in breaks between light pulses, with the secondary light source being switched on.

From every image taken, lines are read out from the monochromatic optical area sensor. These read-out lines have a line pitch relative to each other by which or by a multiple of which line pitch the projection of the object onto the area sensor moves along between consecutive light pulses and optionally secondary light pictures. The line pitch or a multiple thereof, respectively, is thus proportional to the distance for which the object moves along at the conveying speed between consecutive light pulses and optionally secondary light pictures. It will be appreciated that, in this image processing, only a few lines of each image are required for the evaluation, which minimizes the amount of data to be processed.

In order to improve the evaluation of the images, preferably at least so many lines of each image are read out and temporarily stored as there are light pulses different in intensity and/or pulse duration and/or colours and optionally secondary light.

It should be noted that, in most use cases, the secondary light is allowed to shine substantially longer than the light pulses. The secondary light source can be operated intermittently or, moreover, can be in continuous operation. As a result, requirements which are essential for the technical implementation of a secondary light source and for pulsed light sources are inapplicable. Necessary preheating times and a slow switching behaviour are properties which disqualify a light source for the operation as a pulsed light source. For the operation as a secondary light source, such properties are absolutely acceptable. Due to the possible longer operation of the secondary light source, secondary effects can also be utilized which require a longer excitation than the one which would be feasible by pulsed light sources. In the intermittent operation, the on-state of the secondary light source preferably lasts for a multiple of the light duration of the longest light pulse.

The temporarily stored lines from images taken under illumination by the light pulses and optionally illumination by the secondary light source are combined sequentially to form combination lines, with the lines combined with each other having the aforesaid line pitch or a multiple thereof, respectively, relative to each other. The combination lines can be assembled into a combinatory overall picture.

By means of this process according to the invention, images are obtained which were taken under different illuminations. Thus, it is possible to combine individual lines of these images such that combination lines with optimum image information are obtained. Combining can thereby comprise, e.g., adding line information and/or assessing lines of an image as higher or lower, respectively, with regard to lines of other images, wherein assessing as higher or lower, respectively, may extend as far as to the selection of lines of an image and the rejection of lines of other images, e.g., in highly overexposed or underexposed images.

Via very short and not very intense light pulses, respectively, it is possible to detect bright fragments without overloading the area sensor. Via long and/or intense light pulses, dark glasses can be distinguished from porcelain and stone. As a result, it is possible, for example, to identify glasses of a greatly varying light transmittance (from completely transparent to very opaque and darkly coloured) in a material stream with high precision, in particular also if the entire transmission ratio of all glasses is larger than the dynamic range of the monochromatic optical area sensor.

When using the secondary light source the light of which induces an optically detectable secondary effect in objects, an additional information is obtained which serves for an even better material identification.

In a further development of the invention, the light of the individual light pulses has different wavelengths. In case of using pulsed light sources which emit light in the visible wavelength range, each light pulse corresponds to a light colour. This embodiment provides the advantage that each colour component gets directly to the sensor and generates the signals there. By contrast, with colour filter cameras and RGB-illumination as used according to the prior art, the blue and green pixels have no significance for the red light and the red signal component, since the light is absorbed in the colour filter, anyway. The same applies to the other colours. If, in addition, the non-ideal technical implementations of the colour filters with very small pixel sizes, which allow only about 50% of the light quanta to reach the sensor, are taken as a basis, the result according to the invention is a required luminance of the illumination which typically has been reduced to one sixth. A further clear reduction in the requirement for light is achieved by the two-dimensional sensor used according to the invention in that, with every light pulse and, optionally, under secondary light, respectively, several lines are exposed and, subsequently, the lines are assembled sequentially.

Assembling the lines can be done by sequentially combining lines from images which have been taken under consecutive illuminations by light pulses different in intensity and/or pulse duration and/or colours and, optionally, secondary light to form combination lines, wherein the lines to be combined have the defined line pitch or a multiple of said line pitch relative to each other.

Alternatively or additionally, monochromatic lines which have been recorded under equal illuminations at different points in time are sequentially combined to form interlines, in consideration of the time interval between the times of recording and the line pitch within the sequences. Subsequently, interlines allocated to different illuminations are combined to form combination lines, in consideration of the line pitch. The combination lines are in turn assembled into a combinatory overall picture.

A high quality of object detection and a high processing speed are achieved if fast-switching, narrowband to monochromatic light sources, preferably light emitting diodes or lasers, are used for the illumination.

In a preferred embodiment of the invention, the secondary light source is a UV or UV-C light source which stimulates luminescence in objects such as, e.g., lead glass. Thereby, these objects can be distinguished from other objects in a material stream which have the same colour, but cannot luminesce.

In an alternative embodiment of the invention, the secondary light source is a light source with a high proportion of thermal radiation which induces heat absorption in objects. Thus, it is possible to visualize, for example, material-specific cooling effects, wherein the area sensor has to be able to capture heat images.

By illuminating the objects with a narrowband light obtained by filtering, the identification rate is increased, since less extraneous light strikes the objects.

The present invention is particularly suitable for a transmitted light illumination. By transmitted light illumination, transparent or semi-transparent objects are detected and distinguished from non-transparent objects, respectively.

A lighting equipment according to the invention for illuminating objects moved at a conveying speed comprises at least one pulsed light source and optionally at least one secondary light source the light of which induces an optically detectable secondary effect in objects. A casing in which all light sources are incorporated has a light outlet for the passage of the light generated by the light sources, wherein the light outlet is covered by at least one filter glass which dampens in a broadband manner undesirable wavelength ranges of the light generated by the light sources, except for the wavelength ranges which are necessary for identification. By means of this lighting equipment, a high precision in identifying the objects is achievable, since extraneous light is largely eliminated. As a result, for a technical implementation of the invention, the selection of possible light sources is not limited to illuminants of a narrowband radiation characteristic.

In order to be able to detect materials having a high light transmittance as well as those having a very low light transmittance, it is envisaged that the pulsed light sources generate light pulses of different intensities and/or different pulse durations. For high rates of identification, it is suitable if the pulsed light sources are fast-switching, narrowband to monochromatic light sources, preferably light emitting diodes or lasers.

In order to stimulate luminescence in materials, it is envisaged that the secondary light source is a UV or UV-C light source.

In order that colour information regarding the objects can be included in the identification of the objects, in one embodiment of the lighting equipment, it is envisaged that the light sources generate light in different colours in order to illuminate the objects therewith.

The device for the optical detection of moving objects comprises a transport device for conveying the objects, a monochromatic optical area sensor, e.g., a CMOS sensor, comprising a plurality of sensor lines, and a computer for controlling the area sensor and the lighting equipment, with the computer being designed for executing the above-described process according to the invention for the detection of objects.

For the transmitted light operation of the system, it is envisaged that the transport device is translucent and the lighting equipment and the area sensor are positioned on opposite sides of the transport device. However, the system according to the invention is not limited to the transmitted light operation. In particular, it may be convenient to illuminate the objects with the secondary light sources from the same side of the transport device on which the camera is located, i.e., to use the secondary light sources in an incident light operation. However, pulsed light sources can also be arranged on the side of the camera. In particular, it is also possible to position the entire above-described lighting equipment on the side of the camera.

The system according to the invention can be expanded to a material sorting plant by designing the computer for activating a sorting plant depending on the detection of objects to be sorted.

The invention is now illustrated in further detail on the basis of non-limiting exemplary embodiments, with reference to the drawings. In the drawings:

FIG. 5 shows a third path-time course of image recordings by an optical area sensor under illumination by a temporal sequence of light pulses and secondary light as well as the corresponding route of the object in the conveying direction.

Figure 1:
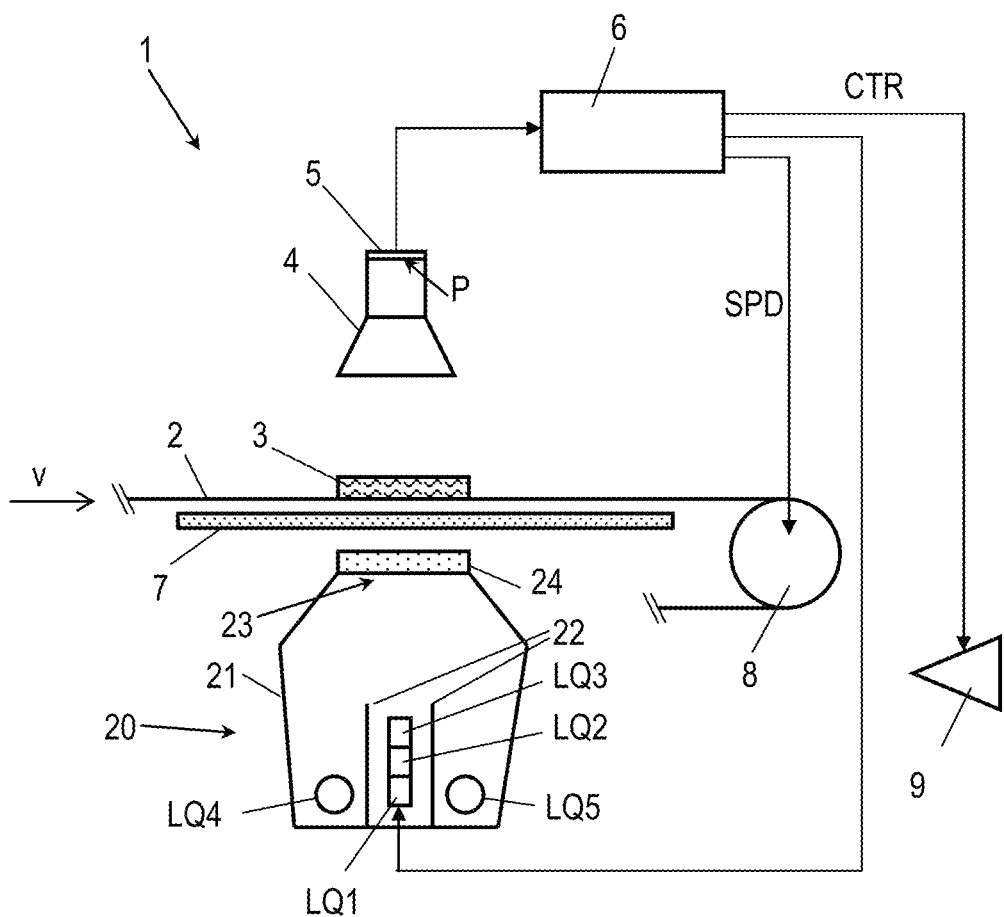
FIG. 1 shows a schematic block diagram of a system according to the invention for the optical detection and subsequent sorting of objects moved at a conveying speed.

With reference to FIG. 1, an exemplary embodiment of a system 1 according to the invention for the optical detection of objects 3 moved at a conveying speed v is now illustrated in further detail. The system 1 comprises a transport device 2 in the form of a conveyor belt. As an alternative, for example, a conveyor chute might also be considered. The transport device 2 is driven by a drive roll 8 at a predetermined conveying speed v. On the transport device 2, an object 3 is conveyed which is to be detected by the system 1. The object is, for example, a transparent piece of glass or plastic which is to be sorted out from a material stream. Alternatively, however, the object 3 may also be a coloured, opaque piece of glass or plastic or a non-transparent part, e.g., a stone, which is to be sorted out from a material stream of glass. However, the applications for the system 1 according to the invention are not limited to the examples illustrated here. A camera 4 comprising a monochromatic (black/white) area sensor 5 for detecting projections P of the object 3 which have been radiated onto the surface of the area sensor 5 by the optical system of the camera 4 is located above the transport device 2. Suitably, the optical axis of the camera 4 is directed at the transport device 2 at right angles. In this connection, it should be mentioned that, in practice, many objects 3 are of course detected simultaneously and that, for a more precise differentiation, usually a plurality of cameras 4 are arranged transversely to the conveying direction of the transport device 2. However, for the purpose of illustrating the invention, only one object 3 and one camera 4 are referred to.

For illuminating the object 3, a lighting equipment 20 according to the invention is provided. The lighting equipment 20 comprises a casing 21 in which three pulsed light sources LQ1, LQ2, LQ3 and two secondary light sources LQ4, LQ5 are arranged. The pulsed light sources LQ1, LQ2, LQ3 are separated from the secondary light sources LQ4, LQ5 by optional dividing walls 21. The use of the dividing walls 21 between the different light sources is not decisive for the detection of objects. If, however, different filter glasses are used for filtering undesirable light portions of the various light sources, filtering can be simplified by dividing walls.

Fast-switching, narrowband to monochromatic light sources, preferably light emitting diodes or lasers, are used as the pulsed light sources LQ1, LQ2, LQ3. The pulsed light sources LQ1, LQ2, LQ3 may all have the same colour (e.g., white) or may emit light in a different colour, e.g., red, green and blue.

In this exemplary embodiment, the secondary light sources LQ4, LQ5 are fluorescent tubes which emit light in the UV or UV-C range. Via UV light, it is possible, for example, to cause lead glass to luminesce; this secondary effect is detectable by the camera 4. Another usable secondary effect is the detection of the cooling behaviour of the object 3. For this purpose, the area sensor 5 must be able to take heat images, and infrared lamps which induce heat absorption in the object 3 are suitably used as secondary light sources LQ4, LQ5.

In one variant of the lighting equipment 20, light pulses of different intensities and/or different pulse durations can be generated with the pulsed light sources LQ1, LQ2, LQ3. Pulses of different intensities can be generated, for example, by simultaneously activating different numbers of (homochromatic) pulsed light sources LQ1, LQ2, LQ3. The pulsed light sources LQ1, LQ2, LQ3 and the secondary light sources LQ4, LQ5 are optionally activated by a computer 6, which is illustrated in further detail below. Note that, for visual reasons, the pulsed light sources LQ1, LQ2, LQ3 are illustrated on top of each other in FIG. 1. However, in practice, they are located horizontally side by side and are suitably integrated in luminaire profiles arranged across the transport device 2.

Figure 2:
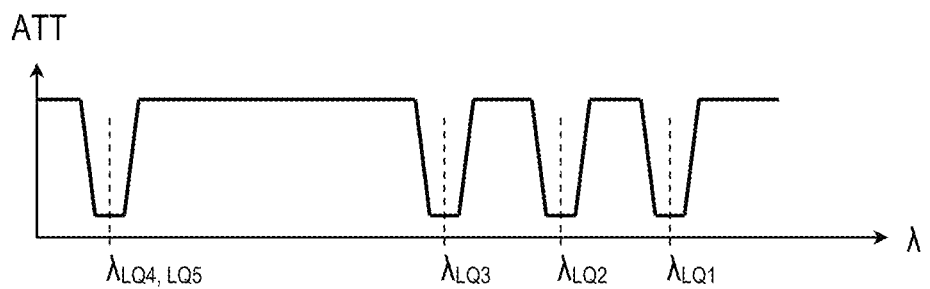
FIG. 2 shows a damping chart depending on the wavelength of a filter glass used in a lighting equipment according to the invention.

The casing 21 comprises a light outlet 23 directed at the transport device 2, which light outlet is covered by a filter glass 24. The filter glass 24 dampens light in a broadband manner, except for light portions with the wavelengths of the light sources LQ1 to LQ5 arranged in the casing 21, which are decisive for the object identification. The damping behaviour of the filter glass 24 is illustrated in the diagram of FIG. 2, assuming by way of example that the pulsed light sources LQ1, LQ2, LQ3 emit red, green and blue light, respectively, and the secondary light sources LQ4, LQ5 emit predominantly UV light. The diagram shows the damping ATT as a function of the wavelength k of the light. It can be seen that, under a light having the wavelengths X(LQ1), k(LQ2) k(LQ3), k(LQ4, LQ5), the damping effect of the filter glass is low, but is high in the remaining wavelength range.

The system 1 according to the invention is intended for operation in a transmitted light process, for which the lighting equipment is arranged below the transport device 2 and the light shines upwards and the camera 4 is arranged above the transport device 2 and detects the light passing through the object 3. For the transmitted light process, it is of course necessary that the transport device 2 is transparent, e.g., comprises a conveyor belt made of a transparent synthetic material. An optional diffuser plate 7 serves for homogenizing the light supplied by the lighting equipment 20.

The monochromatic optical area sensor 5 is designed as an array of sensor dots arranged in lines and columns (typically 1024×1024 pixels), wherein the luminance signals of the pixels can be read out line by line. In a preferred embodiment, the area sensor 5 is designed as a CMOS sensor. The brightness values of the area sensor 5 are read out line by line by a computer 6, are temporarily stored and evaluated according to the detection process according to the invention described below. In this exemplary embodiment, the result of the evaluation is, on the one hand, a control output signal CTR, which activates at least a subsequent sorting device 8, and, on the other hand, a speed control signal SPD, which readjusts the velocity of the drive roll 8.

Figure 3:
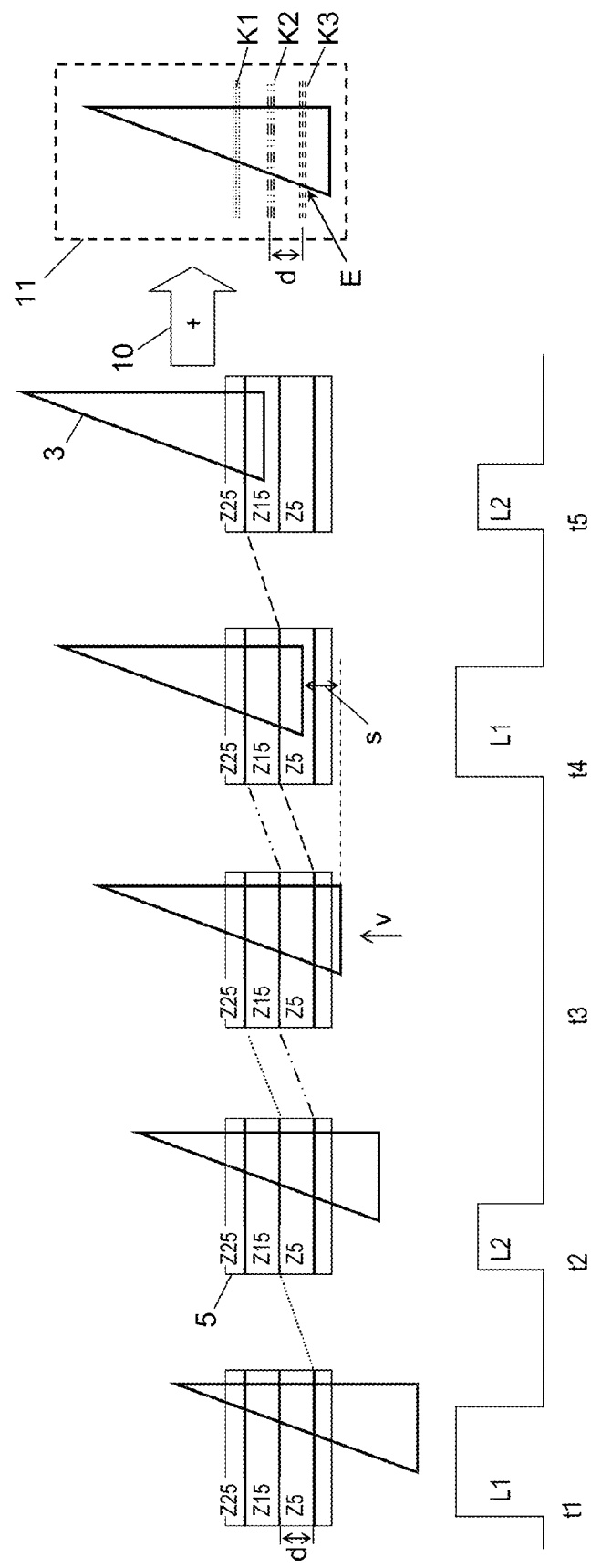
FIG. 3 shows a first path-time course of image recordings by an optical area sensor under illumination by a temporal sequence of light pulses and secondary light as well as the corresponding route of the object in the conveying direction.

Next, the process according to the invention for the optical detection of objects 3, which process is executed in the optical detection system 1, is explained with reference to FIG. 3. FIG. 3 shows top views of the monochromatic area sensor 5 at different instants t1, t2, t3, t4, t5, wherein, for the purpose of simplifying the illustration, it is assumed that it comprises merely 30 sensor lines. Furthermore, FIG. 3 shows the course of the path of the object 3 in the conveying direction (or, to be exact, its projection onto the sensor surface) at instants t1, t2, t3, t4, t5. For the subsequent explanation, the simplifying assumption suffices that the outlines of the real object 3 and of its projection coincide on the surface of the sensor 5 in the drawing due to the optical system of the camera 4.

According to the invention, the object 3 is illuminated with a sequence of one light pulse L1, L2 each at instants t1, t2, t4, t5. Light pulse L1 has a longer pulse duration than light pulse L2. In addition, the intensity of light pulse L1 is larger than that of light pulse L2. The light pulses L1 and L2 have either the same colour or different colours. Light pulse L1 is emitted at instants t1 and t4, light pulse L2 at instants t2 and t5. With the broad, energy-intensive light pulse L1, objects 3 consisting of very dark pieces of broken glass can, for example, be transilluminated. With the weak and short light pulse L2, objects 3 consisting of transparent glass or plastic can be transilluminated without overloading the area sensor 5.

As an optional, but advantageous feature of the system 1, additional information is obtained from a secondary effect detectable on the object 3. For this purpose, the secondary light sources LQ4, LQ5 which provide a secondary light SL are switched on at instant t1 and maintained in continuous operation. At instant t3, a break in the pulsed light occurs, but the secondary light SL continues to be active and thus constitutes the illumination for an image taken by the area sensor 5 at instant t3. The secondary light SL generates an optically detectable secondary effect in the object 3. If, for example, the secondary light SL consists of UV light, an object 3 containing lead glass will luminesce. The luminescing is recorded by the area sensor 5. The sequence of light pulses L1, L2 and pulse breaks in which images are taken under secondary light SL is arbitrary, but constantly repeats itself periodically. In the illustrated exemplary embodiment, the periodic repeat of this sequence occurs with the second light pulse L1 at instant t4.

At instants t1, t2, t3, t4, t5, one image each of the object 3 is taken by the area sensor 5, as is evident under various illuminations by the light pulses L1 and L2 and the secondary light SL, respectively. However, not all lines are read out from this respective image by the computer 6, but only particular ones, namely at least so many lines of each image as there are different light pulses, i.e., three lines in this example. Furthermore, the read-out lines must have a line pitch d relative to each other which corresponds to the distance by which the projection of the object 3 onto the area sensor 5 moves along between consecutive light pulses. This line pitch d is proportional to the distance s for which the real object 3 moves along between consecutive light pulses at the conveying speed v in the conveying direction. It is to be assumed in accordance with practical implementations of the invention that the time intervals between the instants t1, t2, t3, t4, t5 at which the light pulses L1, L2 and the secondary light SL occur in pulse breaks are in each case identical and that the conveying speed v is uniform or variable so slowly, respectively, that a uniform conveying speed between instants t1, t2, t3, t4, t5 can be taken for granted. The result under these conditions is that the line pitch d is constant and, in the present exemplary embodiment, has been determined to comprise 10 lines. Thus, for example, the lines Z5, Z15 and Z25 are read out from each image and are temporarily stored.

Subsequently, the temporarily stored lines from the images taken under illumination with different light pulses L1, L2 and secondary light SL, respectively, at instants t1, t2, t3, t4 and t5 are combined with each other in the computer 6 via a combination algorithm 10 to form combination lines K1, K2, K3, in consideration of the fact that the projection of the object 3 onto the sensor 5 has moved along, in each case, between the individual images by line pitch d. Thus, accordingly, line Z5 of the image taken under illumination by light pulse L1 at instant t1 is combined with line Z15 of the image taken under illumination by light pulse L1 at instant t2 and with line Z25 of the image taken under secondary light SL at instant t3 to form the combination line K1. "Combining", as used herein, can comprise adding the line information, but may also comprise selecting one line information or superimposing two. If the light pulses L1, L2 comprise different colours, each of the lines Z5, Z15 can be regarded as a colour channel for a different colour. If this approach is expanded to three light pulses coloured differently, namely red, green and blue, respectively, the resulting combination line K1 contains the colour information of an RGB image. Analogously, line Z5 of instant t2, line Z15 of instant t3 and line 25 of instant t4 are combined with each other to form the combination line K2. Likewise, line Z5 of instant t3, line Z15 of instant t4 and line Z25 of instant t5 are combined with each other to form the combination line K3. This process is continued until all combination lines have been determined which, in each case, represent a linear section of the object 3 transversely to its conveying direction. The combination lines are assembled into a combinatory overall picture 11 which is examined with regard to sorting criteria. If the combinatory overall picture 11 meets the sorting criteria, the control signal CTR is generated. It should be mentioned that the combination lines K1, K2, K3 etc. of the combinatory overall picture 11 exhibit, in each case, the line pitch d relative to each other. For a higher resolution, it is required to read out more lines from each image and/or to reduce the time intervals between the individual light pulses.

Figure 4:
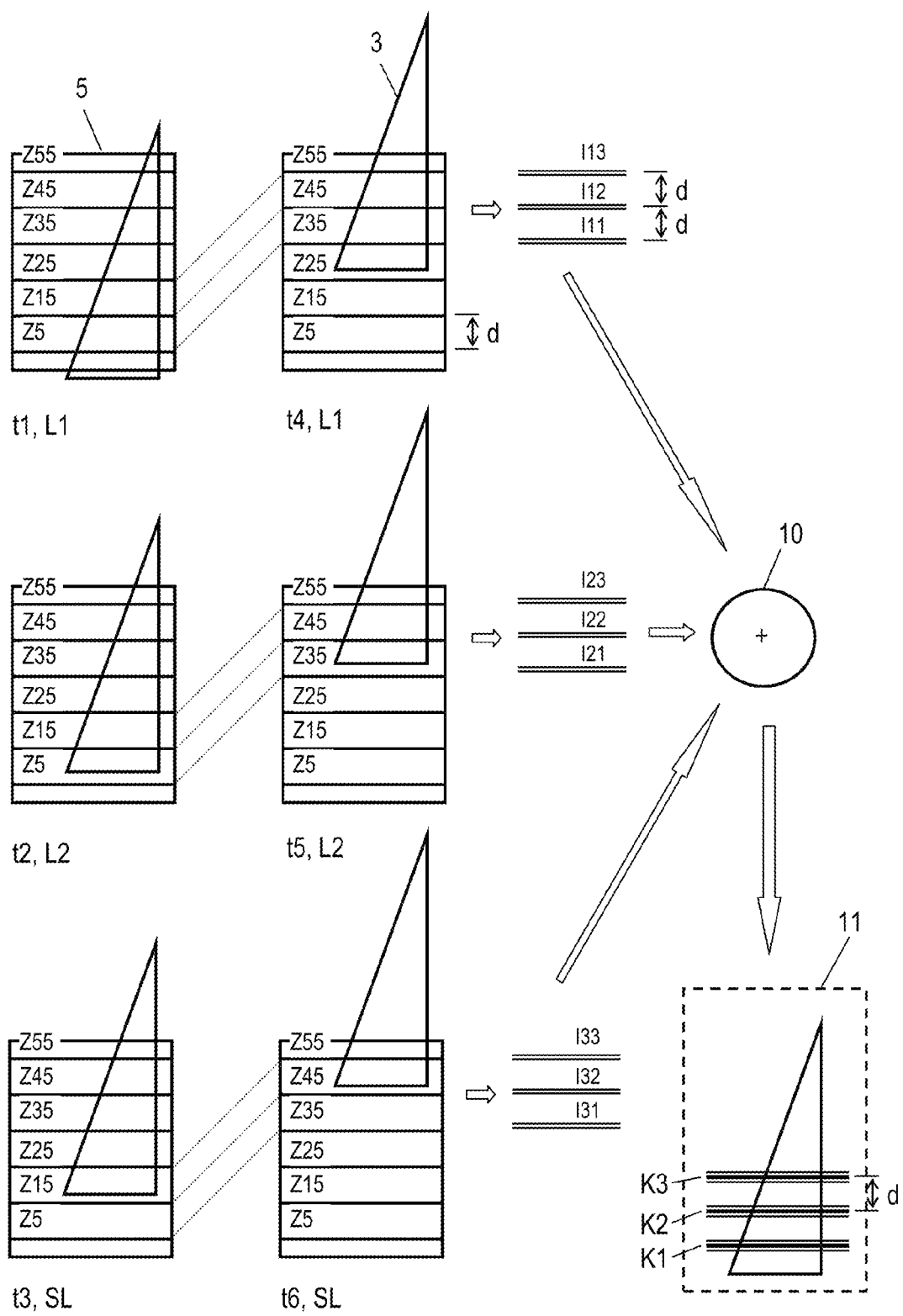
FIG. 4 shows a second path-time course of image recordings by an optical area sensor under illumination by a temporal sequence of light pulses and secondary light as well as the corresponding route of the object in the conveying direction.

On the basis of the diagrams and illustrations of FIG. 4, it is now shown how, by means of the process according to the invention, the luminous intensity necessary for illuminating the object 3 can be reduced down to a fraction. The illustration of FIG. 4 corresponds to that of FIG. 3, except for the difference that two sequences (t1-t3; t4-t6) of light pulses L1, L2 and secondary light SL are illustrated in different colours R, G, B and that, per image taken, twice as many lines as there are different light pulses and secondary light, respectively, for the illumination are read out, i.e., six lines. These are lines Z5, Z15, Z25, Z35, Z45, Z55, which, in each case, have a line pitch d of 10 lines, which has been determined as described above. In contrast to the process described above on the basis of FIG. 3, in the variant of the invention according to FIG. 4, those lines of the two illumination sequences which have been recorded under illumination with equal light pulses or under secondary light, respectively, are initially added to each other in consideration of the fact that the projection of the object 3 moves along from sequence to sequence. For reasons of minimizing the computational effort in the computer 6, the break between the end of one illumination sequence and the beginning of the next illumination sequence has been determined to have the same duration as the time interval between the individual image recordings within one illumination sequence. The line pitch between two sequences is thus 30 lines. This means that the following line additions are performed:

line Z5 of instant t1 and line Z35 of instant t4 to interline I11;

line Z15 of instant t1 and line Z45 of instant t4 to interline I12;

line Z25 of instant t1 and line Z55 of instant t4 to interline I13;

line Z5 of instant t2 and line Z35 of instant t5 to interline I21;

line Z15 of instant t2 and line Z45 of instant t5 to interline I22;

line Z25 of instant t2 and line Z55 of instant t5 to interline I23;

line Z5 of instant t3 and line Z35 of instant t6 to interline I31;

line Z15 of instant t3 and line Z45 of instant t6 to interline I32;

line Z25 of instant t3 and line Z55 of instant t6 to interline I33.

The interlines I11, I12, I13 contain only brightness information of images taken under illumination by the intense light pulse L1.

The interlines I21, I22, I23 contain only brightness information of images taken under illumination by the short, weak light pulse L2.

The interlines I31, I32, I33 contain only brightness information of images taken under secondary light SL.

In the following, the interlines of different illuminations are assembled into combination lines K1, K2, K3 etc. according to the addition algorithm 10 (analogously to FIG. 3), in consideration of the line pitch d. For example, the combination line K1 is assembled from interlines I11, I22, I33. For the combination lines K2 and K3, interlines I12 and I13 are used, however, for the remaining combination lines, interlines which have been detected earlier or future interlines, which, for the sake of clarity, are not illustrated in FIG. 4, would have to be accessed. The combination lines K1, K2, K3 etc. are assembled into a combinatory overall picture 11.

With reference to FIG. 5, it is now shown how, by means of the process according to the invention, significant advantages can be achieved by reading out a larger amount of sensor lines as there are different illuminations. In one use case, a multiple of the object resolution can be achieved with an unchanged image recording frequency. A further use case allows to get by with a fraction of the recording frequency at an unchanged object resolution and, hence, to save a multiplication of the light pulse intervals and thus light energy. The illustration of FIG. 5 corresponds to that of FIG. 3, except for the difference that the time sequence t1'-t5' constitutes twice the time span of the time sequence illustrated in the sequence t1'-t5 of FIG. 3. This is also noticeable from the fact that the distance s' for which the object 3 moves along at the conveying speed v between consecutive light pulses has twice the length of the distance s in FIG. 2, as will be illustrated by means of the following formulae:

$$t2'-t1'=2\times(t2-t1)$$

$$s'=2\times s$$

Furthermore, per image taken, twice as many lines as there are different illuminations are read out, i.e., six lines. These are lines Z5, Z15, Z25, Z35, Z45, Z55, which, in each case, have a line pitch d of 10 lines, which has been determined as described above. The simplifying assumption applies that the detector exhibits merely 60 lines. The recording situation, which is different from FIG. 3, has to be taken into account by an adapted combination algorithm 10'. As a result of the fact that, per illumination (light pulse L1, light pulse L2, secondary light SL), twice as many sensor lines as in the first example are recorded, the combination algorithm 10' also provides twice as many lines recorded under different illuminations as in the above example for the same number of light pulses or the secondary light, respectively. By the combination algorithm 10', line Z15 of the image taken under illumination by the intense light pulse L1 at instant t1' is now combined with line Z35 of the image taken under illumination with the weak light pulse L2 at instant t2' and with line Z55 of the image taken under secondary light SL at instant t3' to form the combination line K1. Analogously, the lines Z5 of t1', Z25 of t2' and Z45 of t3' are combined to form K2, Z15 of t2', Z35 of t3' and Z55 of t4' are combined to form K3, Z5 of t2', Z25 of t3' and Z45 of t4' are combined to form K4, Z15 of t3', Z35 of t4' and Z55 of t5' are combined to form K5, and Z5 of t3', Z25 of t4' and Z45 of t5' are combined to form K6.

The combination lines K1, K2, K3, K4, K5, K6 etc. are assembled into a combinatory overall picture 11.

The invention claimed is:

1. A process for the optical detection of objects moved at a conveying speed, the method comprising:

illuminating an object with one of:

a sequence of light pulses from at least one pulsed light source, the light pulses having different intensities and/or different pulse durations, or a sequence of light pulses from at least one pulsed light source, and a secondary light from a secondary light source, the secondary light source inducing an optically detectable secondary effect in objects;

taking images of the object during each light pulse with a monochromatic optical area sensor comprising a plurality of sensor lines, wherein each image is taken at a different time;

reading out and temporarily storing lines of each image, wherein the read-out lines have a line pitch relative to each other, wherein by the line pitch or a multiple of the line pitch a projection of the object onto the area sensor moves along between consecutive light pulses, the line pitch or a multiple of the line pitch, respectively, being proportional to a distance for which the object moves along at a conveying speed between consecutive light pulses;

sequentially combining lines from different images taken under illumination by the light pulses to form combination lines, with the lines combined with each other having the line pitch or a multiple of the line pitch, respectively, relative to each other; and assembling the combination lines into a combinatory overall picture.

2. A process according to claim 1, wherein taking images of the object during each light pulse with a monochromatic optical area sensor further comprises:

taking images of the object between light pulses under the secondary light.

3. A process according to claim 1, wherein the projection of the object further moves along between consecutive light pulses and an illumination by the secondary light and wherein the object moves along at the conveying speed between consecutive light pulses and the illumination by the secondary light.

4. A process according to claim 1, wherein the light pulses have different wavelengths and/or colours.

5. A process according to claim 4, wherein there are at least as many lines of each image read out and temporarily stored as there are light pulses different in intensity and/or pulse duration and/or colours.

6. A process according to claim 4, wherein there are at least as many lines of each image read out and temporarily stored as there are light pulses different in intensity and/or pulse duration and/or colours and secondary light.

7. A process according to claim 5, wherein the sequence of taking images of the object under illumination by the light pulses is adjusted such that the projection of the object between two light pulses moves along by the line pitch or by an integral multiple of the line pitch between the lines to be read out, wherein lines from images taken with a sequence of illuminations by light pulses different in intensity and/or pulse duration and/or colours are combined sequentially to form combination lines with the lines to be combined having the line pitch or a multiple thereof relative to each other.

8. A process according to claim 5, wherein the sequence of taking images of the object under illumination by the light pulses and in pulse breaks between pulses under secondary light is adjusted such that the projection of the object between two light pulses or between light pulses and light breaks moves along by the line pitch or by an integral multiple of the line pitch between the lines to be read out, wherein lines from images taken with a sequence of illuminations by light pulses different in intensity and/or pulse duration and/or colours are combined sequentially to form combination lines with the lines to be combined having the line pitch or a multiple thereof relative to each other.

9. A process according to claim 5, further comprising reading out and temporarily storing at least twice as many lines of each image as there are different illuminations which result from light pulses different in intensity and/or pulse duration and/or colours and sequentially combining those monochromatic lines which have been recorded under equal illuminations at different instants to form interlines in consideration of the time interval between the image recording times and the line pitch within the illumination sequence, as well as subsequently combining the interlines allocated to different illuminations to form combination lines in consideration of the line pitch and assembling the combination lines into a combinatory overall picture.

10. A process according to claim 1, wherein fast-switching, narrowband to monochromatic light sources are used as the pulsed light sources.

11. A process according to claim 1, wherein the secondary light source is a UV or UV-C light source which stimulates luminescence in objects.

12. A process according to claim 1, wherein the secondary light source is a light source with a high proportion of thermal radiation which induces heat absorption in objects.

13. A process according to claim 1, wherein the objects are illuminated by filtering with narrowband light.

14. A process according to claim 1, wherein the object is moved on a transparent transport device and the illumination of the object occurs through the transport device, with the optical area sensor being positioned on the same side of the transport device as is the object.

15. Lighting equipment for illuminating objects moved at a conveying speed comprising:

light sources including a pulsed light source configured to illuminate objects with one of:

a sequence of light pulses from the at least one pulsed light source, the light pulses having different intensities and/or different pulse durations, or a sequence of light pulses from the at least one pulsed light source, and a secondary light from a secondary light source, the secondary light source inducing an optically detectable secondary effect in objects;

a casing in which all light sources are incorporated, the casing including a light outlet for the passage of light generated by the light sources, wherein the light outlet is covered by at least one filter glass which dampens in a broadband manner light of the light sources arranged in the casing, except for light portions which are necessary for detection;

an area sensor that generates an image during more than one of the light pulses included in the sequence of light pulses, wherein each image is taken at a different time; and a computer configured to combine lines from different images to form a combinatory overall picture.

16. Lighting equipment in accordance with claim 15, further comprising at least one secondary light source, the secondary light source producing light which induces detectable secondary effects in objects.

17. Lighting equipment according to claim 15, wherein the pulsed light sources are operable in order to generate light pulses of different intensities and/or different pulse durations.

18. Lighting equipment according to claim 15, wherein the pulsed light sources are fast-switching, narrowband to monochromatic light sources.

19. Lighting equipment according to claim 16, wherein the secondary light source is a UV or UV-C light source.

20. Lighting equipment according to claim 16, wherein the light sources generate light of different wavelengths/colours.

21. A device for the optical detection of objects moved at a conveying speed, comprising:

a transport device for conveying the objects;

lighting equipment, the lighting equipment including at least one pulsed light source and a casing, wherein the at least one pulsed light source is incorporated in the casing, wherein the casing includes a light outlet for the passage of light generated by the at least one light source, wherein the light outlet is covered by at least one filter glass which dampens in a broadband manner light of the at least one light source arranged in the casing, except for light portions which are necessary for detection;

a monochromatic optical area sensor comprising a plurality of sensor lines; and a computer for controlling the area sensor and the lighting equipment, wherein the objects are by detected by:
  illuminating the objects with one of:
    a sequence of light pulses from the at least one pulsed light source, the light pulses having different intensities and/or different pulse durations, or
    a sequence of light pulses from the at least one pulsed light source, and a secondary light from a secondary light source, the secondary light source inducing an optically detectable secondary effect in objects;
  taking images of the objects during each light pulse with the monochromatic optical area sensor, wherein each image is taken at a different time;
  reading out and temporarily storing lines of each image, wherein the read-out lines have a line pitch relative to each other, wherein by the line pitch or a multiple of the line pitch a projection of the objects onto the area sensor moves along between consecutive light pulses, the line pitch or a multiple of the line pitch, respectively, being proportional to a distance for which the objects move along at a conveying speed between consecutive light pulses;
  sequentially combining lines from different images taken under illumination by the light pulses to form combination lines, with the lines combined with each other having the line pitch or a multiple of the line pitch, respectively, relative to each other; and
  assembling the combination lines into a combinatory overall picture.

22. A device according to claim 21, wherein the transport device is translucent and the lighting equipment and the area sensor are positioned on opposite sides of the transport device.

23. A device according to claim 21, wherein the computer is designed for activating a sorting plant.

* * * * *